United States Patent [19]

Burkhart et al.

[11] Patent Number: 5,565,194
[45] Date of Patent: Oct. 15, 1996

[54] POLYSILOXANE-POLYOXYALKYLENE BLOCK COPOLYMERS AND THEIR USE AS ADDITIVES FOR HAIR COSMETICS

[75] Inventors: Georg Burkhart, Essen; Rolf-Dieter Langenhagen, Hattingen; Andreas Weir, Essen; Volker Zellmer, Bottrop, all of Germany

[73] Assignee: TH. Goldschmidt AG., Essen, Germany

[21] Appl. No.: 558,860

[22] Filed: Nov. 15, 1995

Related U.S. Application Data

[63] Continuation-in-part of Ser. No. 398,482, Mar. 3, 1995, abandoned.

[30] Foreign Application Priority Data

Mar. 4, 1994 [DE] Germany .......................... 44 07 189.2

[51] Int. Cl.⁶ .............................. A61K 7/06; C08G 77/14
[52] U.S. Cl. ...................... 424/70.12; 556/445; 556/446; 528/15; 528/31; 528/29; 525/474; 510/122; 510/466
[58] Field of Search .................... 556/445, 446; 528/15, 31, 29; 424/70.12; 525/474; 252/174.15, DIG. 13

[56] References Cited

U.S. PATENT DOCUMENTS

| | | | |
|---|---|---|---|
| 4,070,386 | 1/1978 | Rossmy | 260/448.8 R |
| 4,532,132 | 7/1985 | Keil | 514/772 |
| 5,059,704 | 10/1991 | Petroff et al. | 556/437 |
| 5,104,998 | 4/1992 | Ichinohe | 556/445 |
| 5,145,879 | 9/1992 | Budnik et al. | 521/112 |
| 5,159,096 | 10/1992 | Austin et al. | 556/445 |
| 5,260,469 | 11/1993 | Swiatek | 556/445 |
| 5,306,737 | 4/1994 | Buckhart et al. | 521/112 |
| 5,401,870 | 3/1995 | Raleigh et al. | 556/445 |

FOREIGN PATENT DOCUMENTS

| | | |
|---|---|---|
| 0275563 | 7/1988 | European Pat. Off. . |
| 1012602 | 7/1957 | Germany . |
| 1570647 | 2/1971 | Germany . |
| 1694366 | 6/1971 | Germany . |
| 1795557 | 3/1972 | Germany . |
| 2541865 | 4/1976 | Germany . |
| 3133869 | 5/1983 | Germany . |

*Primary Examiner*—Margaret W. Glass
*Attorney, Agent, or Firm*—Anderson, Kill, Olick P.C.

[57] ABSTRACT

The invention relates to polysiloxanes with 1) at least two polyether groups A and B, polyoxyalkylene group, with an average molecular weight of 600 to 5,500, consisting of 20 to 100% by weight of oxyethylene units and of 80 to 0% by weight of oxypropylene units and the polyoxyalkylene group B, with an average molecular weight of 700 to 5,000, consisting of 0 to <20% by weight of oxyethylene units and of 100 to 80% by weight of oxypropylene units, and with 2) hydrocarbon groups with 6 to 30 carbon atoms, linked to silicon. The invention further relates to the synthesis of these polysiloxanes and their use as additives for hair cosmetics, particularly as additives for hair shampoos to improve the handle and the combability of the hair.

9 Claims, No Drawings

POLYSILOXANE-POLYOXYALKYLENE BLOCK COPOLYMERS AND THEIR USE AS ADDITIVES FOR HAIR COSMETICS

This is a continuation-in-part application of Ser. No. 08/398,482, filed Mar. 3, 1995, now abandoned.

FIELD OF INVENTION

The invention relates to polysiloxane-polyoxyalkylene block copolymers, their synthesis, and a method of improving the handle and combability of a hair cosmetic by adding an effective amount of the inventive block copolymers particularly to hair shampoos.

BACKGROUND INFORMATION AND PRIOR ART

A wide range of applications has been found for polyoxyalkylene-polysiloxane block copolymers, which are referred to in the following as polyethersiloxanes. They can be used as surfactants, emulsifiers, dispersants, leveling agents for paints, lubricants, auxiliary materials for the tertiary recovery of crude oil, as foam stabilizers in polyurethane foaming, as a textile auxiliary for brightening fibers, yarns or sheet-like textile products, for hydrophilizing sanitary products of textile fibers and for many other purposes.

The polyethersiloxanes therefore have manifold uses, since their properties, particularly their hydrophilic/-hydrophobic balance, can be influenced and brought to the desired value by selecting a suitable siloxane block or siloxane blocks on the one hand, and constructing the polyether block or blocks appropriately on the other.

For example, the siloxane block can be linear or branched, and the absolute number of difunctional and trifunctional siloxy units and their numerical ratio to one another can be varied within wide limits.

Aside from the polyether blocks, it is also possible to link other modifying groups to a silicon atom. Examples of such groups are long-chain hydrocarbon groups with up to 30 carbon atoms, hydrocarbon groups substituted with halogen atoms, cyano groups or polar groups, hydroxyl groups, etc.

The polyether groups can likewise have different structures. Each polyoxyalkylene block may be composed of different oxyalkylene units, primarily of oxyethylene, oxypropylene and oxybutylene units. Moreover, the molecular weight ratio of these units to one another, as well as the molecular weight of the polyoxyalkylene block, can be varied. The end group of the polyoxyalkylene block, which can be reactive (for example, an OH group) or inert (for example, an alkoxy group), is also of importance.

The polyoxyalkylene block can be linked to the polysiloxane block by a hydrolytically stable C—Si bond or by a hydrolytically less stable C—O—Si bond.

It is also possible and, for many applications, desirable to link different polyether blocks to the polysiloxane block. In this connection, the different polyether blocks differ with respect to their molecular weight and/or their hydrophilicity and/or their inert or reactive end groups.

Polysiloxanes with different polyether blocks are described, for instance, in the following patents and published patent applications:

German Patent 15 70 647: Chloropolysiloxanyl sulfates are reacted with mixtures of alkylene oxide adducts, which consist of 50 to 95 OH equivalent percent of polyalkylene glycol monoethers comprising ethylene oxide and propylene oxide units, contain 40 to 70 mole percent of oxypropylene units and have a molecular weight ($M_n$) of 1,000 to 3,000, and the hydroxyl groups of which preferably are secondary, and of 5 to 50 OH equivalent of alkylene oxide adducts of polyhydric hydroxyl compounds with a molecular weight ($M_n$) of 130 to 3500, the polyalkylene glycol components of which consist of ethylene oxide and/or propylene oxide units and which have an OH equivalent weight of up to 1750, and the hydroxyl groups of which preferably are secondary, the quantitative ratios being chosen so that there is at most 1.4 and, preferably, 1.05 to 1.2 OH equivalents for each acid equivalent of the chloropolysiloxanyl sulfate.

German Patent 16 94 366: This patent relates to polysiloxane-polyoxyalkylene block copolymers, the polysiloxane block of which has a conventional structure and the polyoxyalkylene block of which, however, consists of 25 to 70% by weight of a polyoxyalkylene with an average molecular weight ($M_n$) of 1,600 to 4,000 and an ethylene oxide content of 20 to 100% by weight, the remainder being propylene oxide and, optionally, higher alkylene oxides, and 30 to 75% by weight of a polyoxyalkylene with an average molecular weight ($M_n$) of 400 to 1,200 and an ethylene oxide content of 65 to 100% by weight, the remainder being propylene oxide and, optionally, higher alkylene oxides.

German Offenlegungschrift 25 41 865: The polysiloxane-polyoxyalkylene block copolymers are defined with respect to their polyoxyalkylene block so that one polyoxyalkylene block has an average molecular weight ($M_n$) of 900 to 1,300 and consists of 30 to 55% by weight of ethylene oxide, the remainder being propylene oxide, and the other polyoxyalkylene block has an average molecular weight ($M_n$) of 3,800 to 5,000 and consists of 30 to 50% by weight of ethylene oxide, the remainder being propylene oxide.

European Publication 0 275 563: The block copolymer, described in this published European patent application, comprises three different polyoxyalkylene blocks, namely one block which contains 20 to 60% by weight of oxyethylene units and has a molecular weight ($M_n$) of 3,000 to 5,500, another block with 20 to 60% by weight of oxyethylene units and a molecular weight ($M_n$) of 800 to 2,900, and a third block which contains only polyoxy-propylene units and has a molecular weight of ($M_n$) 130 to 1200.

According to the state of the art, such polyether-siloxanes can be prepared in various ways. In this connection, reference is made to the following patents:

German Patent 10 12 602: Monohydric and dihydric polyether alcohols are reacted in the presence of a solvent and a catalyst with polysiloxanes, which have terminal ≡Si—O-alkyl groups, the aliphatic alcohol set free being distilled off from the reaction mixture. The reaction therefore is a trans-esterification reaction.

German Patent 17 95 557: Equilibrated siloxane mixtures having the general formula $R_xSiO_y(SO_4)_zX_{4-(z+2x+2y)}$, wherein R is any univalent hydrocarbon group, X represents a halogen or alkoxy group, x has a value of 0.9 to 2.2, y has a value of 0.75 to 1.75 and z has a value of 0.0001 to 0.5, with the proviso that $4 > (x+2y+2x) > 2$, are reacted with monohydric polyether, the acid set free during the reaction is neutralized and the reaction product is filtered off and freed from solvent.

By both methods, polyethersiloxanes are obtained in which the polyether group(s) is (are) linked to the siloxane backbone over an Si—O—C bond.

The synthesis of polyethersiloxanes, in which the polyether groups(s) is (are) linked to the siloxane backbone over an Si—C bond, is given in the German patent 31 33 869. According to the method described there, allyl polyethers are reacted with polysiloxanes, which have SiH groups, in the presence of special platinum catalysts and, optionally, in the presence of inert solvents.

The invention is concerned with the technical problem of finding polyethersiloxanes, which are particularly suitable for use in hair cosmetics and can be used, in particular, as additives for hair shampoos. At the same time, a further aim is to improve the handle and the combability of the hair.

OBJECT OF THE INVENTION

An object of the present invention is inventive polysiloxane-polyoxyalkylene block copolymers. Another object of the invention is a method of synthesizing the inventive block copolymers. Yet another object of the invention is an additive for hair cosmetics comprising the inventive block copolymers and a method for improving the handle and combability of hair by applying an effective amount of the block copolymers.

SUMMARY OF THE INVENTION

The present invention thus relates to new polysiloxane-polyoxyalkylene block copolymers of the general formula

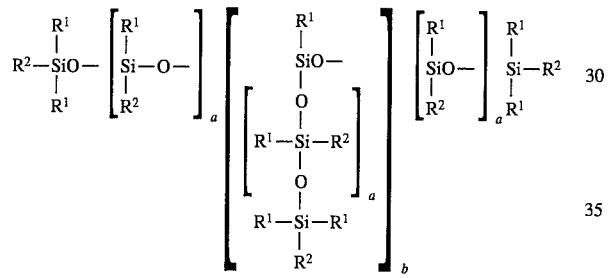

wherein $R^1$ represents alkyl groups with 1 to 4 carbon atoms or phenyl groups, with the proviso that at least 90% of the $R^1$ groups are methyl groups, $R^2$
  (1) corresponds to the $R^1$ groups, or
  (2) represents groups with 6 to 30 carbon atoms, obtained by the addition reaction between hydrocarbons with an olefinic double bond and the SiH groups of the siloxane, or
  (3) —M—$R^3$ groups, wherein
    M is a divalent group having the formula —$R^4_x$O—, in which the $R^4$ is a divalent alkylene group, which can also be branched, and x has a value of 0 or 1, $R^3$ is a mixture of polyether groups, which contains at least one
  (1a) polyoxyalkylene group A with an average molecular weight ($M_n$) of 600 to 5,500, which consists of 20 to 100% by weight of oxyethylene units and 80 to 0% by weight of oxypropylene units, and one
  (2a) polyoxyalkylene group B with an average molecular weight ($M_n$) of 700 to 5,000, which consists of 0 to < 20% by weight of oxyethylene units and 100 to 80% by weight of oxypropylene units, it being possible to replace up to 20% by weight of the oxypropylene units by oxybutylene units and the molar ratio of the polyoxyalkylene groups A to the polyoxyalkylene groups B being 1:4 to 4:1, with the proviso that
  (I) the number of $R^2$ groups having the meaning (2) is at least equal to 1 and, at most, to 30% of the numerical value of the number of silicon atoms, and
  (II) there are at least two $R^3$ groups in the average block copolymer, b has a value of 0 to 10, a has a value of 10 to 100, when b=0, or a value of 3 to 70, when b>0 and ≦4, or a value of 3 to 30, when b>4.

An essential characteristic of the present invention is the simultaneous presence of the hydrocarbon groups with 6 to 30 carbon atoms and the polyoxyalkylene groups, which are connected with the polysiloxane backbone, as well as the nature and amount of these groups.

Preferably, $R^1$ is a methyl group. In the majority of the groups, $R^2$ corresponds to $R^1$. It is, however, an essential characteristic of the invention that some of the $R^2$ groups are groups with 6 to 30 carbon atoms, obtained by the addition reaction between hydrocarbons with an olefinic double bond and the SiH group of the siloxane.

The following are preferred examples of such hydrocarbon groups:

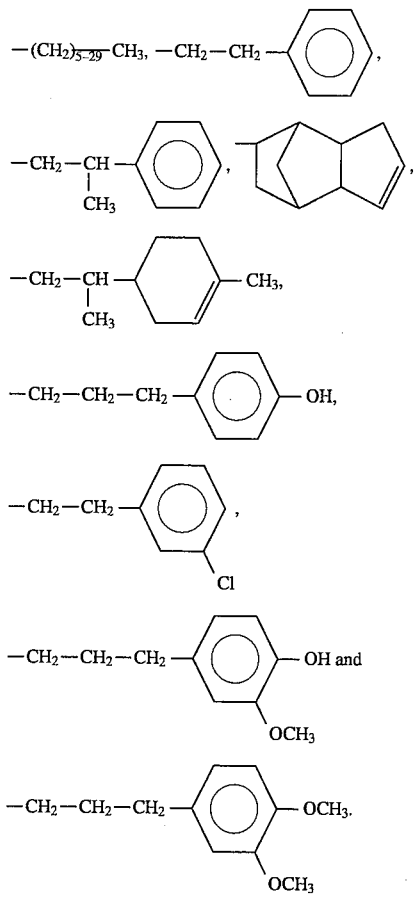

Furthermore, $R^2$ groups may be groups having the formula —$R^4_x$O—.

Preferably, the $R^4$ group is a —$(CH_2)_2$— or —$(CH_2)_3$— group.

The polyoxyalkylene blocks preferably correspond to the formula —$(C_mH_{2m}O-)_nR^5$, conditions concerning the composition and the respective molecular weight of the different polyoxyalkylene blocks are fulfilled. $R^5$ is an alkyl group with 1 to 4 carbon atoms, an acyl group or an —O—CO—NH—R⁶ group, wherein R⁶ is an alkyl or aryl group.

Independently of one another, the A and B polyoxyalkylene groups preferably have an average molecular weight ($M_n$) of 1,000 to 4,000.

The A and B blocks may be contained several times and be linked to a common average molecule. In the event that the A and B polyoxyalkylene groups are contained several times, the polyoxyalkylene groups of the individual types of blocks need not be identical to one another. The A and B polyether groups must correspond only to the respective conditions for the individual types of blocks.

Preferably, the molar ratio of the A polyoxyalkylene groups to the B polyoxyalkylene groups is 1:3 to 3:1.

The inventive block copolymers can be synthesized by known methods, a differentiation being made depending on whether the polyether blocks are linked by Si—C— or by Si—O—C— bonds with the polysiloxane.

The following method is particularly preferred for synthesizing the inventive compounds with Si—C— bonds:

Organopolysiloxanes of the general formula molar ratio of 1:4 to 4:1, are reacted consecutively or simultaneously by a hydrosilylating addition reaction in the presence of platinum catalysts, which are suitable for the hydrosilylation, such as hexachloroplatinic acid.

It is thus possible to first add the olefinic hydrocarbons to the hydrogensiloxane and then the polyether mixture to the remaining SiH groups or to carry out both addition reactions simultaneously.

A further preferred method relates to the synthesis of the inventive compounds with Si—O—C bonds. This method is characterized in that organopolysiloxanes of the general formula

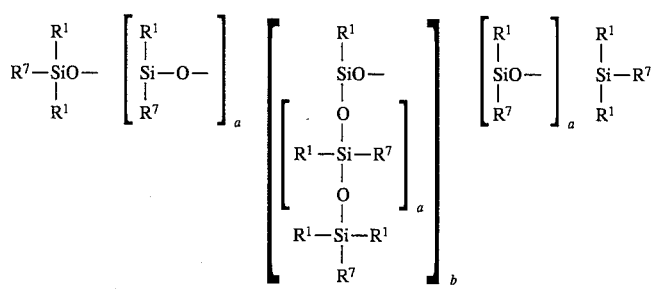

wherein

R¹ and the subscripts a and b have the meaning already given,

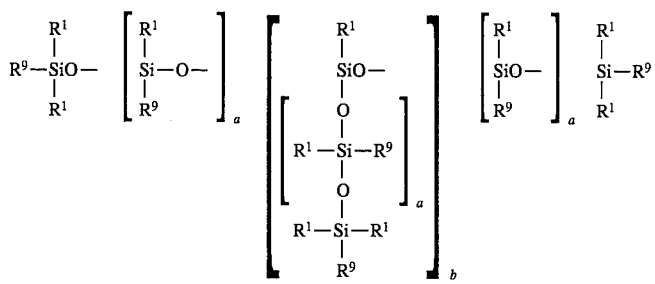

wherein

R¹ and the subscripts a and b have the meaning already given,

R⁹

(1) corresponds to the R¹ groups, or
(2) represents groups with 6 to 30 carbon atoms, which are obtained by the addition reaction between hydrocarbons with an olefinic double bond and the SiH groups of the siloxane, or
(3) represents halogen or other acidic groups such as —SO$_{4/2}$ OR —CH$_3$SO$_3$, with the proviso that at least one R⁹ group has the meaning given in (2) and at least two R⁹ groups have the meaning given in (3), are reacted in the presence of an acid acceptor at a temperature not less than 50° C. with such an amount of a mixture of the polyethers

R⁷

(1) corresponds to R¹ groups, or
(2) is a SiH group, with the proviso that at least three R⁷ groups are SiH groups,
 a) hydrocarbons with 6 to 30 carbon atoms and an olefinic double bond, and
 b) a mixture of polyethers having the formula

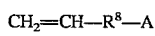

and

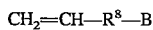

wherein the R⁸ group corresponds to the R⁴ group minus the —(CH$_2$)$_2$— group and the polyethers are present in the

A—OH and

B—OH, which are present in a molar ratio of 1:4 to 4:1, that at least two polyether groups are linked to the desired organopolysiloxane.

Suitable acid acceptors are, for example, ammonia gas, triethylamine and i-propylamine.

The inventive compounds show the desired properties as additive for hair cosmetics. It is therefore a further object of the invention to use the inventive compounds as additives for hair cosmetics, particularly for hair shampoos, in amounts of 0.5 to 4% by weight, based on the total amount of the shampoos, to improve the handle and the combability of the hair.

In the following examples, the compounds below are used, it being understood that the Examples are provided by way of illustration and not by way of limitation.

Siloxanes:

I) $(CH_3)_3SiO—((CH_3)_2SiO—)_{58}((CH_3)HSiO—)_9Si(CH_3)_3$

II) $H(CH_3)_2SiO—((CH_3)_2SiO—)_{80}((CH_3)HSiO—)_8Si(CH_3)_2H$

III) $(CH_3)_3SiO—((CH_3)_2SiO—)_{130}((CH_3)HSiO—)_{18}Si(CH_3)_3$

IV) $(CH_3)_3SiO—((CH_3)_2SiO—)_{100}((CH_3)HSiO—)_{12}Si(CH_3)_3$

V)

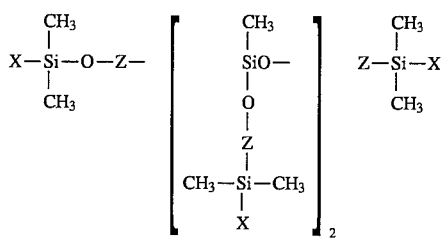

wherein $Z=—((CH_3)_2SiO—)_7((CH_3)(C_8H_{17})SiO—)$, and

X=75% Cl and 25% $SO_{4/2}$.

Polyethers of Type A:

a) $CH_2=CH—CH_2O—(C_2H_4O—)_{12}CH_3$
b) $CH_2=CH—CH_2O—(C_2H_4O—)_{12}H$
c) $CH_2=CH—CH_2O—(C_2H_4O—)_{21}CH_3$
d) $C_4H_9O—(C_2H_4O—)_{12}H$
e) $C_4H_9O—(C_2H_4O—)_{82}(C_3H_6O—)_{5.4}H$
f) $CH_2=CH—CH_2O—(C_2H_4O—)_{45}(C_3H_6O—)_{34}CH_3$
g) $CH_2=CH—CH_2O—(C_2H_4O—)_{42}(C_3H_6O—)_{34}COCH_3$
h) $CH_2=CH—CH_2O—(C_2H_4O—)_{46}(C_3H_6O—)_{16}CH_3$
i) $CH_2=CH—CH_2O—(C_2H_4O—)_{16}(C_3H_6O—)_{12}CH_3$
k) $CH_2=CH—CH_2O—(C_2H_4O—)_{45}(C_3H_6O—)_{34}H$
l) $C_4H_9O—(C_2H_4O—)_{23}(C_3H_6O—)_{33}H$

Polyethers of Type B:

m) $CH_2=CH—CH_2O—(C_2H_4O—)_5(C_3H_6O—)_{21}CH_3$
n) $CH_2=CH—CH_2O—(C_2H_4O—)_2(C_3H_6O—)_{32}CH_3$
o) $CH_2=CH—CH_2O—(C_3H_6O—)_{13}CH_3$
p) $C_4H_9O—(C_2H_4O—)_6(C_3H_6O—)_{25}H$

Hydrosilylyzable olefins:

$C_6$=1-hexene
$C_8$=1-octene
$C_{12}$=1-dodecene
$C_{20/24}$=mixture of α-olefins with 20–24 carbon atoms and an average molecular weight ($M_n$) of 301
ST=styrene
AMS=α-methylstyrene
DCPD=dicyclopentadiene
LIM=limonene
ALPH=allylphenol
VBC=vinylbenzyl chloride

EXAMPLE 1

To a flask equipped with a stirrer, thermometer, gas inlet and distillation head, 18.7 g (0.0188 moles) of polyether c), 150.9 g (0.0375 moles) of polyether f), 47.2 g (0.0313 moles) of polyether m) and 320 mL of toluene are added.

Toluene (150 mL) is distilled off in a nitrogen atmosphere for the azeotropic drying of the polyether mixture. After that, the flask is equipped with a reflux condenser and further, nitrogen is passed through the apparatus. At a temperature of 105° C., 6.3 g (0.375 moles) of 1-dodecene and 55.6 g (0.1 mole of SiH) of siloxane I are added to the flask.

After a thorough mixing of the flask contents, 0.18 g of a 10% solution of $H_2PtCl_6 \cdot 6H_2O$ in i-propanol are added. The mixture is allowed to react out for 3.5 hours, after which time an SiH conversion of 97.8% is attained (determined by the hydrogen that can be split off in an alkaline medium with n-butanol). The mixture is treated with 3 g of bentonite, stirred for 30 minutes and filtered. Subsequently, the toluene is distilled off at 80° C. and 20 mbar. A clear, yellowish product is obtained.

EXAMPLES 2 TO 12

The following products have been synthesized under the conditions of Example 1 (see Table). As a catalyst, $H_2PtCl_6 \cdot 6H_2O$ is used. About 0.7 g of a 10% solution of $H_2PtCl_6 \cdot 6H_2O$ in i-propanol are employed per 1000 g of formulation (siloxane+polyether). Toluene (300 to 800 mL per 1,000 g of formulation) is used as solvent for the reactions.

| | Siloxane | | | Polyether | | | Olefin | | | Conversion |
|---|---|---|---|---|---|---|---|---|---|---|
| Examples | Type | g | Moles SiH | Type | g | Moles | Type | g | Moles | in % |
| 2 | II | 65.5 | 0.1 | a | 7.5 | 0.0125 | C16 | 7.0 | 0.0313 | 99.5 |
| | | | | f | 201.2 | 0.05 | | | | |
| | | | | m | 47.2 | 0.0313 | | | | |
| 3 | III | 60.5 | 0.1 | c | 12.5 | 0.0125 | C6 | 3.7 | 0.0438 | 99.3 |
| | | | | h | 37.8 | 0.0125 | | | | |
| | | | | i | 27.6 | 0.0188 | | | | |
| | | | | n | 75.6 | 0.0375 | | | | |
| 4 | IV | 69.2 | 0.1 | a | 7.5 | 0.0125 | C20 | 9.4 | 0.0313 | 98.3 |
| | | | | i | 27.6 | 0.0188 | C24 | | | |
| | | | | k | 50.1 | 0.0125 | | | | |

| Examples | Siloxane Type | g | Moles SiH | Polyether Type | g | Moles | Olefin Type | g | Moles | Conversion in % |
|---|---|---|---|---|---|---|---|---|---|---|
| 5 | III | 60.5 | 0.1 | m | 75.5 | 0.05 | ST | 2.6 | 0.025 | 97.4 |
|   |   |   |   | c | 12.5 | 0.0125 |   |   |   |   |
|   |   |   |   | g | 98.0 | 0.125 |   |   |   |   |
|   |   |   |   | i | 18.4 | 0.0125 |   |   |   |   |
|   |   |   |   | o | 41.3 | 0.05 |   |   |   |   |
| 6 | III | 60.5 | 0.1 | b | 7.3 | 0.0125 | AMS | 3.0 | 0.025 | 98.9 |
|   |   |   |   | f | 201.2 | 0.05 |   |   |   |   |
|   |   |   |   | m | 56.6 | 0.0375 |   |   |   |   |
| 7 | II | 65.5 | 0.1 | a | 7.5 | 0.0125 | DCPD | 4.1 | 0.0313 | 97.1 |
|   |   |   |   | h | 56.7 | 0.0188 |   |   |   |   |
|   |   |   |   | k | 75.2 | 0.0188 |   |   |   |   |
|   |   |   |   | m | 66.1 | 0.0438 |   |   |   |   |
| 8 | III | 60.5 | 0.1 | a | 11.3 | 0.0188 | LIM | 4.3 | 0.0313 | 99.3 |
|   |   |   |   | f | 176.1 | 0.0438 |   |   |   |   |
|   |   |   |   | m | 47.2 | 0.0313 |   |   |   |   |
| 9 | III | 60.5 | 0.1 | a | 11.3 | 0.0188 | ALPH | 4.2 | 0.0313 | 98.7 |
|   |   |   |   | f | 176.1 | 0.0438 |   |   |   |   |
|   |   |   |   | m | 47.2 | 0.0313 |   |   |   |   |
| 10 | III | 60.5 | 0.1 | a | 11.3 | 0.0188 | VBC | 4.8 | 0.0313 | 98.9 |
|   |   |   |   | f | 176.1 | 0.0438 |   |   |   |   |
|   |   |   |   | m | 47.2 | 0.0313 |   |   |   |   |
| 11 | III | 60.5 | 0.1 | a | 7.5 | 0.0125 | C12 | 8.4 | 0.05 | 99.1 |
|   |   |   |   | f | 150.9 | 0.0375 |   |   |   |   |
|   |   |   |   | m | 37.8 | 0.025 |   |   |   |   |
| 12 | III | 60.5 | 0.1 | c | 12.5 | 0.0125 | C8 | 4.2 | 0.375 | 97.9 |
|   |   |   |   | h | 56.7 | 0.0188 | LIM | 3.4 | 0.025 |   |
|   |   |   |   | k | 50.1 | 0.0125 |   |   |   |   |
|   |   |   |   | n | 37.8 | 0.0188 |   |   |   |   |

EXAMPLE 13

To a flask equipped with a stirrer, thermometer, gas inlet and stillhead, 13.2 g (0.022 moles) of polyether d), 87.9 g (0.022 moles) of polyether e), 66.0 g (0.022 moles) of polyether 1), 78.7 g (0.044 moles) of polyether p) and 1,100 mL of toluene are added. Toluene (150 mL) is distilled off in a nitrogen atmosphere for the azeotropic drying of the polyether mixture. At 50° C., the stillhead is exchanged for a reflux condenser. Subsequently, 83 g (0.1 moles of SiX) of siloxane V are added. Ammonia gas is then passed in at 60° C. until the contents of the flask react positively for ammonia. The reaction is allowed to continue for a further hour, the passing in of ammonia being continued at a greatly reduced rate. The precipitated salt is subsequently filtered off. After that, the toluene is distilled off at 70° C. and 20 mbar. A light brown, almost clear product is obtained.

EXAMPLE 14

(not of the invention)

Polyether a) (7.5 g, 0.0125 moles), 301.8 g (0.075 moles) of polyether f) and 56.6 g (0.0375 moles) of polyether m) are reacted under the conditions of Examples 2 to 12 with 65.5 g (0.1 moles of SiH) of siloxane II. The SiH conversion is 99.4%.

TESTING THE APPLICATION

The above-described properties were found in comparison trials of conditioning shampoos on strands of Indo-European human hair:

For this purpose, in each case

| 2.0% | of the polyethersiloxane to be tested with |
| 3.0% | of TEGOSOFT GC (glycerin cocoate with 7 moles of ethylene oxide) |
| 40.0% | of Texapon N 25 (lauryl ether sulfate) |
| 43.2% | of water |
| 10.0% | of TEGO betaine F 50 (cocosoamidopropylbetaine) |
| 1.3% | of ANTIL 171 (thickener), and |
| 0.5% | of NaCl | were mixed into a shampoo formulation.

In the comparison test, grades are awarded from zero to four, zero being the worst (deficient) and four the best (very good) rating. By comparing the seven shampoos with one another, the following grades, averaged over ten candidates, were obtained.

|  | PRODUCT OF EXAMPLE |  |  |  |  |  | ABIL B 8852 |
|---|---|---|---|---|---|---|---|
|  | 2 | 3 | 4 | 8 | 12 | 14 |  |
| In Wet Hair |  |  |  |  |  |  |  |
| Knotting | 2.5 | 2.3 | 2.5 | 2.4 | 2.5 | 2.2 | 2.2 |
| Combability | 2.2 | 2.2 | 2.3 | 2.3 | 2.2 | 1.9 | 2.2 |
| Handle | 2.2 | 2.2 | 2.3 | 2.2 | 2.3 | 2.2 | 2.2 |
| In Dry Hair |  |  |  |  |  |  |  |
| Combability | 3.0 | 3.0 | 3.1 | 3.0 | 3.1 | 2.8 | 2.8 |
| Handle | 2.6 | 2.6 | 2.8 | 2.7 | 2.6 | 1.8 | 1.8 |
| Gloss | 2.2 | 2.1 | 2.2 | 2.2 | 2.2 | 2.0 | 2.0 |

The products of Examples 2, 3, 4, 8 and 12 are of the invention.

The product of Example 14 and ABIL B 8852 (a commercial product of Th. Goldschmidt AG) are not of the invention.

In this comparison, particularly the handle of the dry hair, is rated better when treated with the shampoo of the inventive compounds of Examples 2, 3, 4, 8 and 12 than when treated with the products of the comparison examples, which are not of the invention. The knotting and the combability of the wet hair are also rated somewhat better after treatment

8. The additive of claim 7, wherein the hair cosmetic is a hair shampoo and the block copolymer is present in an amount of 0.5 to 4% by weight, based on the total amount of shampoo.
9. The additive of claim 7, wherein $R^2$ is selected from the group consisting of
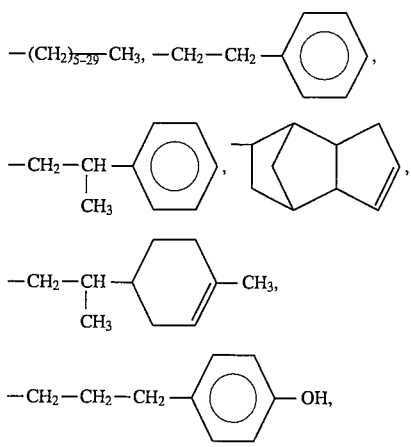
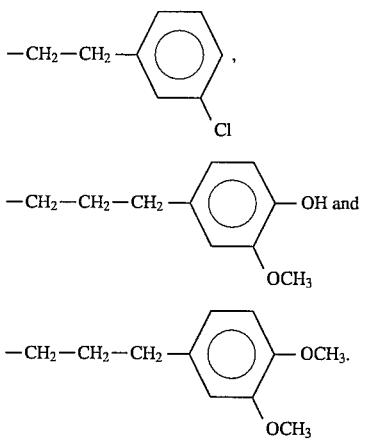

We claim:

1. A polysiloxane-polyoxyalkylene block copolymer of the general formula

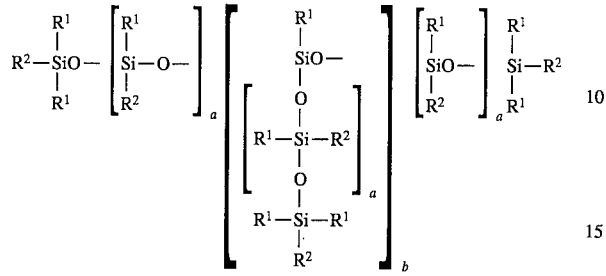

wherein $R^1$ represents alkyl groups with 1 to 4 carbon atoms or phenyl groups, with the proviso that at least 90% of the $R^1$ groups are methyl groups, $R^2$ (1) corresponds to the $R^1$ groups, or (2) represents groups with 6 to 30 carbon atoms, obtained by the addition reaction between hydrogen and carbon containing compounds having an olefinic double bond and SiH groups, or (3) represents —M—$R^3$ groups, wherein M is a divalent group having the formula —$R^4_xO$—, in which $R^4$ is a divalent alkylene group, which is branched or unbranched, and x has a value of 0 or 1, $R^3$ represents at least one group (1a) and at least one group (2a) where (1a) is a polyoxyalkylene group A with an average molecular weight ($M_n$) of 600 to 5,500, which consists of 20 to 100% by weight of oxyethylene units and 80 to 0% by weight of oxypropylene units, and (2a) is a polyoxyalkylene group B with an average molecular weight ($M_n$) of 700 to 5,000, which consists of 0 to 20% by weight of oxyethylene units and 100 to 80% by weight of oxypropylene units, wherein optionally up to 20% by weight of the oxypropylene units is replaced by oxybutylene units and the molar ratio of the polyoxyalkylene groups A to the polyoxyalkylene groups B being 1:4 to 4:1, with the proviso that (I) the number of $R^2$ groups having the meaning (2) above, is at least equal to 1% and, at most, to 30% of the numerical value of the number of silicon atoms, and (II) there is at least one polyoxyalkylene group A and at least one polyoxyalkylene group B in the average block copolymer, b has a value of 0 to 10, a has a value of 10 to 100, when b=0, or a value of 3 to 70, when b>0 and ≦4, or a value of 3 to 30, when b>4.

2. The block copolymers of claim 1, wherein the $R^2$ group in (2) is selected from the group consisting of

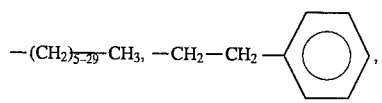

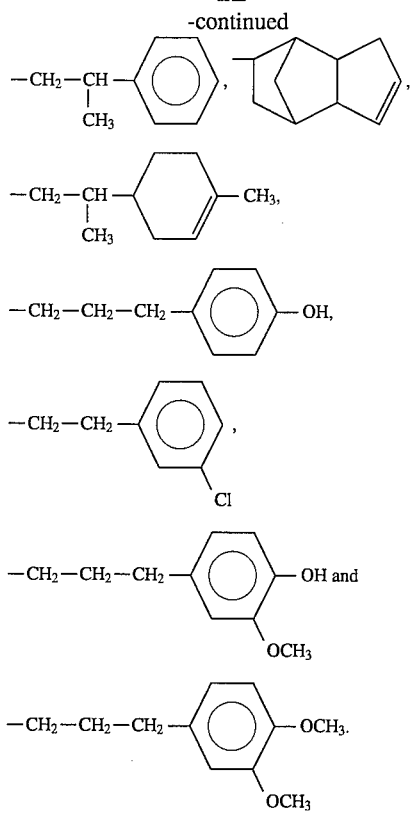

3. The block copolymers of either claim 1 or 2, wherein the polyoxyalkylene blocks correspond to the formula —$(C_mH_{2m}O—)_nR^5$, the subscripts n and m being selected so that conditions concerning composition and the respective molecular weight of the different polyoxyalkylene blocks are fulfilled, $R^5$ being an alkyl group with 1 to 4 carbon atoms, an acyl group or an —O—CO—NH—$R^6$ group, wherein $R^6$ is an alkyl or aryl group.

4. A method of improving the handle and the combability of hair, comprising adding an effective amount of a block copolymer of the general formula

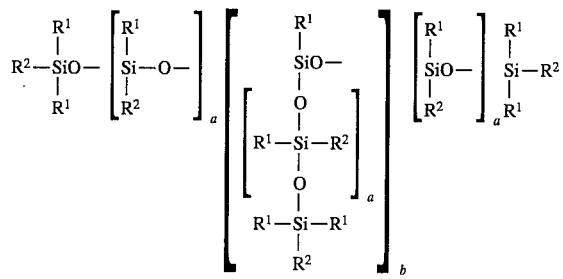

wherein $R^1$ represents alkyl groups with 1 to 4 carbon atoms or phenyl groups, with the proviso that at least 90% of the $R^1$ groups are methyl groups, $R^2$ (1) corresponds to the $R^1$ groups, or (2) represents groups with 6 to 30 carbon atoms, obtained by the addition reaction between hydrogen and carbon containing compounds having an olefinic double bond and SiH groups, or (3) represents —M—$R^3$ groups, wherein M is a divalent group having the formula —$R^4_xO$—,
in which $R^4$ is a divalent alkylene group, which is branched or unbranched, and x has a value of 0 or 1, $R^3$ represents at least one group (1a) and at least one group (2a) where
   (1a) is a polyoxyalkylene group A with an average molecular weight ($M_n$) of 600 to 5,500, which consists of 20 to 100% by weight of oxyethylene units and 80 to 0% by weight of oxypropylene units, and
   (2a) is a polyoxyalkylene group B with an average molecular weight ($M_n$) of 700 to 5,000, which consists of 0 to 20% by weight of oxyethylene units and 100 to 80% by weight of oxypropylene units, wherein optionally up to 20% by weight of the oxypropylene units is replaced by oxybutylene units and the molar ratio of the polyoxyalkylene groups A to the polyoxyalkylene groups B being 1:4 to 4:1, with the proviso that
   (I) the number of $R^2$ groups having the meaning (2) above, is at least equal to 1% and, at most, to 30% of the numerical value of the number of silicon atoms, and
   (II) there are at least two $R^3$ groups in the average block copolymer, b has a value of 0 to 10, a has a value of 10 to 100, when b=0, or a value of 3 to 70, when b>0 and ≦4, or a value of 3 to 30, when b>4, to a hair cosmetic and applying the said hair cosmetic to the hair so as to improve the handle and combability of the hair.

5. The method of claim 4, wherein the hair cosmetic is a hair shampoo and the effective amount of the block copolymer is 0.5 to 4% by weight, based on the total amount of shampoo.

6. The method of claim 4, wherein $R^2$ is selected from the group consisting of

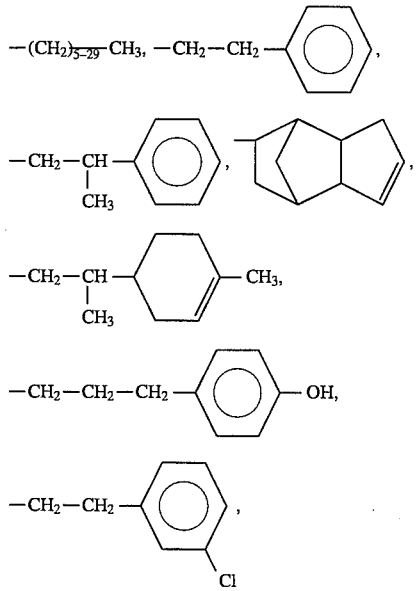

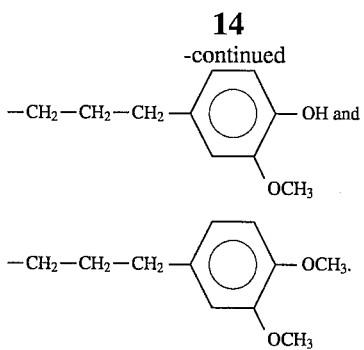

7. An additive for a hair cosmetic comprising a block copolymer of the general formula

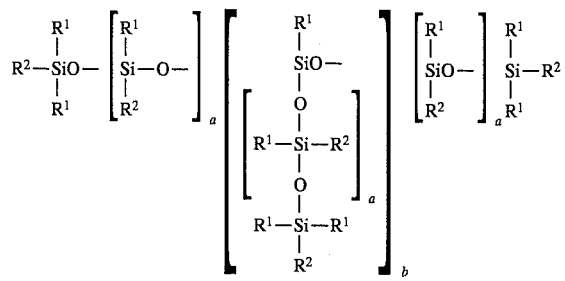

wherein
$R^1$ represents alkyl groups with 1 to 4 carbon atoms or phenyl groups, with the proviso that at least 90% of the $R^1$ groups are methyl groups, $R^2$
   (1) corresponds to the $R^1$ groups, or
   (2) represents groups with 6 to 30 carbon atoms, obtained by the addition reaction between hydrogen and carbon containing compounds having an olefinic double bond and SiH groups, or
   (3) represents —M—$R^3$ groups, wherein
      M is a divalent group having the formula —$R^4_xO$—, in which $R^4$ is a divalent alkylene group, which is branched or unbranched, and x has a value of 0 or 1, $R^3$ represents at least one group (1a) and at least one group (2a) where
   (1a) is a polyoxyalkylene group A with an average molecular weight ($M_n$) of 600 to 5,500, which consists of 20 to 100% by weight of oxyethylene units and 80 to 0% by weight of oxypropylene units, and
   (2a) is a polyoxyalkylene group B with an average molecular weight ($M_n$) of 700 to 5,000, which consists of 0 to 20% by weight of oxyethylene units and 100 to 80% by weight of oxypropylene units, where optionally up to 20% by weight of the oxypropylene units is replaced by oxybutylene units and the molar ratio of the polyoxyalkylene groups A to the polyoxyalkylene groups B being 1:4 to 4:1, with the proviso that
   (I) the number of $R^2$ groups having the meaning (2) above, is at least equal to 1% and, at most, to 30% of the numerical value of the number of silicon atoms, and
   (II) there are at least two $R^3$ groups in the average block copolymer, b has a value of 0 to 10, a has a value of 10 to 100, when b=0, or a value of 3 to 70, when b>0 and ≦4, or a value of 3 to 30, when b>4.